US010459111B2

(12) United States Patent
Arodzero et al.

(10) Patent No.: US 10,459,111 B2
(45) Date of Patent: Oct. 29, 2019

(54) SYSTEM AND METHOD FOR ADAPTIVE X-RAY CARGO INSPECTION

(71) Applicant: Radiabeam Technologies, LLC, Santa Monica, CA (US)

(72) Inventors: Anatoli Arodzero, Billerica, MA (US); Salime Max Boucher, Santa Monica, CA (US); Alex Murokh, Encino, CA (US); Sergey Vinogradov, Warrington (GB); Sergey Kutsaev, Santa Monica, CA (US)

(73) Assignee: RadiaBeam Technologies, LLC, Santa Monica, CA (US)

( * ) Notice: Subject to any disclaimer, the term of this patent is extended or adjusted under 35 U.S.C. 154(b) by 0 days.

(21) Appl. No.: 14/720,751

(22) Filed: May 23, 2015

(65) Prior Publication Data
US 2015/0338545 A1 Nov. 26, 2015

Related U.S. Application Data

(60) Provisional application No. 62/002,379, filed on May 23, 2014.

(51) Int. Cl.
*G01V 5/00* (2006.01)
*G01T 1/20* (2006.01)
(Continued)

(52) U.S. Cl.
CPC ........... *G01V 5/0041* (2013.01); *G01N 23/02* (2013.01); *G01N 23/04* (2013.01); *G01T 1/20* (2013.01);
(Continued)

(58) Field of Classification Search
None
See application file for complete search history.

(56) References Cited

U.S. PATENT DOCUMENTS

| 4,809,314 A * | 2/1989 | Steele | G01B 7/285 378/145 |
|---|---|---|---|
| 5,524,133 A * | 6/1996 | Neale | G01V 5/0041 250/393 |

(Continued)

FOREIGN PATENT DOCUMENTS

WO  WO-2008121072 A1 * 10/2008 ........... H01L 31/107

OTHER PUBLICATIONS

Vinogradov et al., "Performance of X-ray detectors with SiPM readout in cargo accelerator-based inspection systems", IEEE (Year: 2013).*

*Primary Examiner* — Michael J Logie
(74) *Attorney, Agent, or Firm* — Sunstein Kann Murphy & Timbers LLP

(57) ABSTRACT

An X-ray based inspection systems providing radiographic imaging for cargo inspection and material discrimination with adaptive control dependent upon characteristics of the cargo under inspection. A packet of X-ray pulses with controllable packet duration is produced that allows multi-energy material discrimination in a single scan line and real-time adjustment of packet duration to adapt to cargo attenuation. In addition, adaptive dynamic adjustment of the operational characteristic of the detector channels increases the effective dynamic range and as a result increases the penetration and range of thicknesses where material discrimination is possible. The material discrimination technique is applied within a single packet of short pulses of several hundred nanoseconds. Feedback from the detection system is used to control the packet duration of each packet of X-ray pulses in order to adapt scan parameters to the object that is being imaged.

11 Claims, 14 Drawing Sheets

(51) Int. Cl.
*G01T 1/22* (2006.01)
*G01N 23/02* (2006.01)
*G01T 1/24* (2006.01)
*G01N 23/04* (2018.01)

(52) U.S. Cl.
CPC ............... *G01T 1/22* (2013.01); *G01T 1/248* (2013.01); *G01V 5/00* (2013.01); *G01N 2223/423* (2013.01); *G01N 2223/505* (2013.01); *G01N 2223/639* (2013.01)

(56) References Cited

U.S. PATENT DOCUMENTS

| | | | | |
|---|---|---|---|---|
| 5,838,759 | A * | 11/1998 | Armistead | B66C 19/007 378/57 |
| 7,453,987 | B1 * | 11/2008 | Richardson | G01V 5/0041 378/57 |
| 7,957,505 | B1 * | 6/2011 | Katz | G01B 15/00 378/147 |
| 8,023,619 | B2 * | 9/2011 | McNabb, Jr. | G01V 5/0016 378/106 |
| 8,457,274 | B2 | 6/2013 | Arodzero et al. | |
| 9,218,933 | B2 * | 12/2015 | Langeveld | H01J 37/1472 |
| 9,404,875 | B2 | 8/2016 | Langeveld | |
| 2003/0016790 | A1 * | 1/2003 | Grodzins | G01N 23/02 378/147 |
| 2006/0008052 | A1 * | 1/2006 | Elyan | G01N 23/04 378/57 |
| 2007/0183568 | A1 * | 8/2007 | Kang | A61B 6/4241 378/57 |
| 2010/0034355 | A1 * | 2/2010 | Langeveld | G01N 23/02 378/95 |
| 2011/0038453 | A1 * | 2/2011 | Morton | G01V 5/0016 378/57 |
| 2011/0163236 | A1 * | 7/2011 | Arodzero | G01V 5/0008 250/361 R |
| 2012/0093289 | A1 * | 4/2012 | Arodzero | G01V 5/0041 378/57 |
| 2013/0136230 | A1 * | 5/2013 | Arodzero | G01N 23/02 378/57 |
| 2013/0208857 | A1 * | 8/2013 | Arodzero | G01T 1/2006 378/57 |
| 2013/0230139 | A1 * | 9/2013 | Morton | G01V 5/0066 378/57 |
| 2014/0192958 | A1 * | 7/2014 | Dinca | G01V 5/0016 378/64 |
| 2014/0270086 | A1 * | 9/2014 | Krasnykh | H05G 2/00 378/124 |
| 2014/0294147 | A1 * | 10/2014 | Chen | G01V 5/0016 378/57 |
| 2015/0139386 | A1 * | 5/2015 | Star-Lack | G01V 5/0016 378/57 |
| 2017/0055338 | A1 * | 2/2017 | Saverskiy | H05H 7/02 |

* cited by examiner

SYSTEM AND METHOD FOR ADAPTIVE X-RAY CARGO INSPECTION

CROSS-REFERENCE TO RELATED APPLICATIONS

This application claims the benefit of U.S. Provisional Application No. 62/002,379 titled "System and Method for High Speed, Intelligent X-ray Cargo Inspection" filed May 23, 2014. The entire disclosure of the above application is incorporated herein by reference.

FIELD OF THE INVENTION

The present disclosure relates generally to methods and apparatus for cargo inspection and, more particularly, to X-ray based inspection systems providing radiographic imaging and material discrimination with adaptive control dependent upon characteristics of the cargo under inspection.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As used herein the terms "pixel" or "detector pixel" refer to a detector element without regard to the associated electronics. As used herein the term "detector channel" refers to a detector pixel, e.g. the sensitive volume of a scintillation crystal in conjunction with its photodetector, e.g. a Silicon Photomultiplier (SiPM) and its associated front-end-electronics.

As used herein the term "cumulative saturation" refers to saturation that is not due to a short intensive light flash, but due to a less intensive but continuous light incident on the photodetector (for example, but not limited to, SiPM photodetectors or photomultiplier photodetectors). This cumulative saturation is a result of the recovery time of the photodetectors (for example, but not limited to, SiPM photodetectors or photomultiplier photodetectors).

X-ray security systems for the inspection of cargo and shipping containers typically use transmission radiographic techniques based on use an X-ray fan beam generated by a pulsed high-energy X-ray source 110, such as a linear accelerator, linac. FIG. 1 (prior art) depicts a cargo inspection system employing such a technique.

A fan-shaped beam of X-ray 116, emitted by a source, linac or betatron based, for example, is detected by elements of a detector array 118 distal to a target object, here a cargo container 20, in order to produce radiographic images of the target object 190. The particular contents of the object may be discriminated and characterized on the basis of the transmission of X-rays through the object and its detection by the detector array and its individual detector pixels. Signals from each of the detector pixels, suitably pre-processed, provide inputs to processors, where radiographic image of object and material characteristics are computed. The thickness of the material to be penetrated by the X-rays may exceed 400 mm of steel equivalent in some cases. To insure the required penetration, inspection systems typically use X-rays with a maximum energy of several MeV, currently up to about 9 MeV. X-rays in excess of 1 MeV are frequently referred to as hard X-rays or high-energy X-rays.

Information (such as mass absorption coefficient, effective atomic number $Z_{eff}$, electron density, etc.) with respect to the material composition of the contents of objects may be obtained on the basis of the interaction of X-rays with the material, and, more particularly, by illuminating the material with X-ray beams having energy spectra with more than one distinct energy endpoint (peak energy), or by employing energy discriminating detectors. Dual energy methods of material discrimination are widely used in X-ray inspection systems for security control of cargo in checkpoints. Dual energy inspection is discussed in the following references, for example, which are incorporated herein by reference:

W. Neale, et al., "Material Identification using X-Rays". U.S. Pat. No. 5,524,133. (1996).

V. Novikov, et al. "Dual energy method of material recognition in high energy introscopy systems". International Workshop on Charged Particle Linear Accelerators: Problems of Atomic Science and Technology, pp. 93-95 (1999).

S. Ogorodnikov, et al. "Application of high-penetrating introscopy systems for recognition of materials". Proceedings of EPAC 2000, Vienna, Austria. pp. 2583-2585.

S. Ogorodnikov and V. Petrunin. Processing of interlaced image in 4-10 MeV dual energy customs systems for material recognition. In: Physical review special topics—Accelerators and beams, Vol. 5, 104701 (2002), 11p.

P. Bjorkholm. "Dual energy radiation scanning of objects" International Patent WO 2005/084352 (2005).

Prior art examples of the methods of high speed X-ray cargo inspection utilized Scintillation-Cherenkov detection approach was introduced in US Patent Application 2011/0163236 (by A. Arodzero), incorporated herein by reference.

Another recently proposed method is intra-pulse multi-energy cargo inspection using the natural intra-pulse variations in X-ray spectrum from conventional linacs, [FIG. 4 of U.S. Pat. No. 8,457,274 by A. Arodzero et al]. The detector signal is separately acquired for multiple time intervals relative to the pulse onset, and processed to obtain values corresponding to multiple-energy analysis of the transmitted radiation. Due to the effect of cumulative saturation of photodetectors (PMT and SiPM) [S. Vinogradov, A. Arodzero, and R. C. Lanza. Performance of X-ray detectors with SiPM readout in accelerator-based cargo inspection systems. 2013 IEEE Nuclear Science Symposium and Medical Imaging Conference, Oct. 27-Nov. 2, 2013, Seoul, Korea. DOI: 10.1109/NSSMIC.2013.6829597], this method (U.S. Pat. No. 8,457,274) only allows material discrimination for a very limited range of material thicknesses. Furthermore, the lack of controllability of the energy variation precludes use in an adaptive technique.

Another prior art example of high speed X-ray cargo inspection, FIG. 2, is the multi-beam inspection method presented in US Patent Application 2013/0136230 (by A. Arodzero and M. Rommel).

Other newer techniques in cargo inspection attempting to provide material discrimination with a non-interlaced, single energy linac, have been proposed, [US Patent Application 2011/0096906 by W. Langeveld]. One such method, direct spectroscopy (Z-Spec), uses an array of small plastic scintillators for gamma-ray spectroscopy in order to provide information about the atomic number of the traversed material. However, this approach remains impractical due to the high count rates needed for imaging large cargo containers.

Another proposed method, noise spectroscopy [W. Langeveld, et al. Noise spectroscopy: Z determination by statistical count-rate analysis (Z-scan). NIM A, 652 (2011) 79-83], provides spectral information indirectly by analyzing statistical fluctuations in the transmitted X-ray signal. A bright, high-Z scintillation detector (LSO or LYSO) with vacuum PMT readout is necessary for this method. The primary drawback is the high cost of these scintillation materials.

There is a need for an adaptable inspection system able to overcome the foregoing deficiencies and provide enhanced material identification adaptable to variable characteristics of the cargo under inspection.

BRIEF DESCRIPTION OF THE DRAWINGS

The various features of the invention will be more readily understood by reference to the following detailed description, taken with reference to the accompanying drawings, in which.

SUMMARY OF EMBODIMENTS OF THE INVENTION

Figure 1:
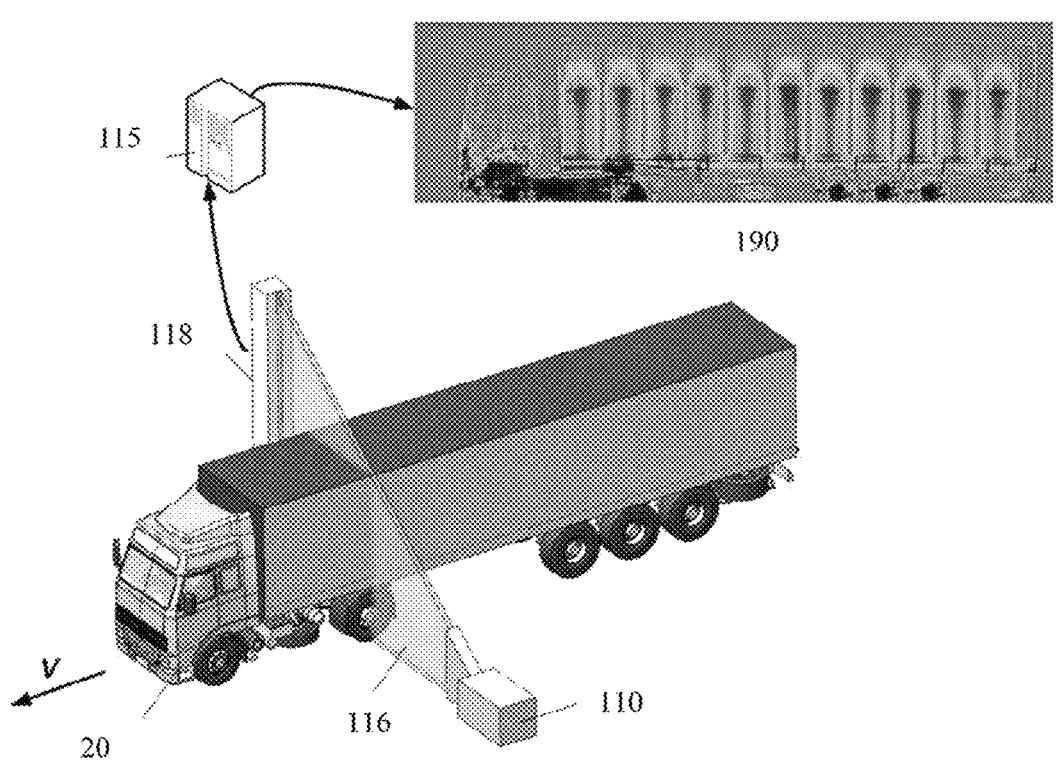
FIG. 1 is a diagram of an example configuration of a cargo x-ray transmission inspection system.
Figure 2:
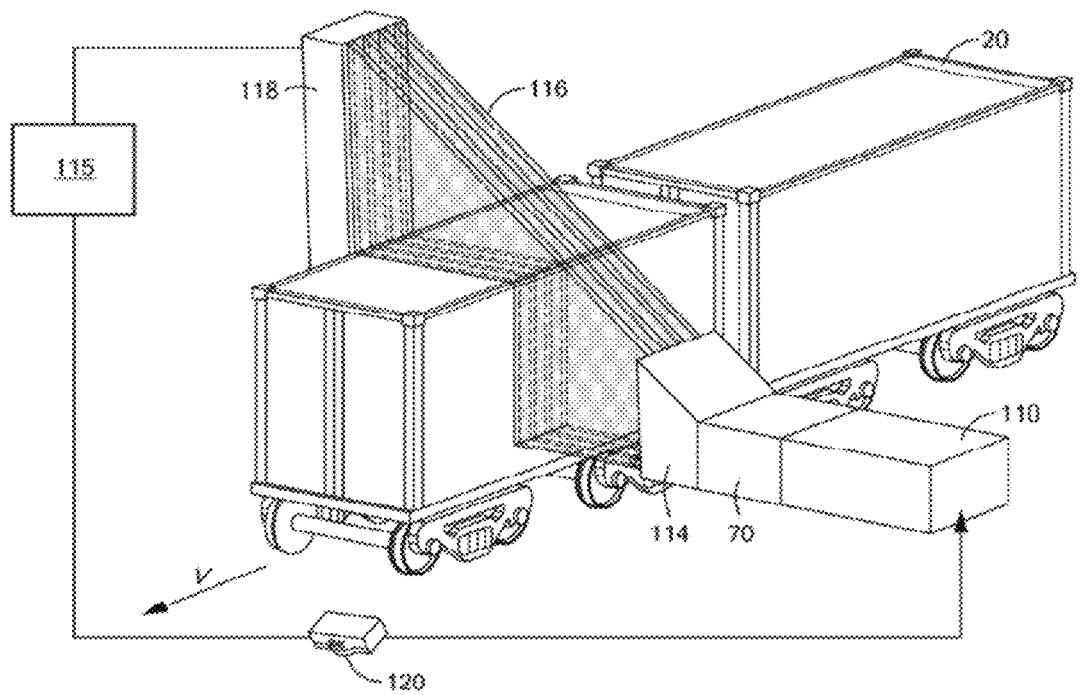
FIG. 2 is a diagram of an example configuration of a cargo x-ray transmission inspection system with multiple transmission beams.
Figure 3:
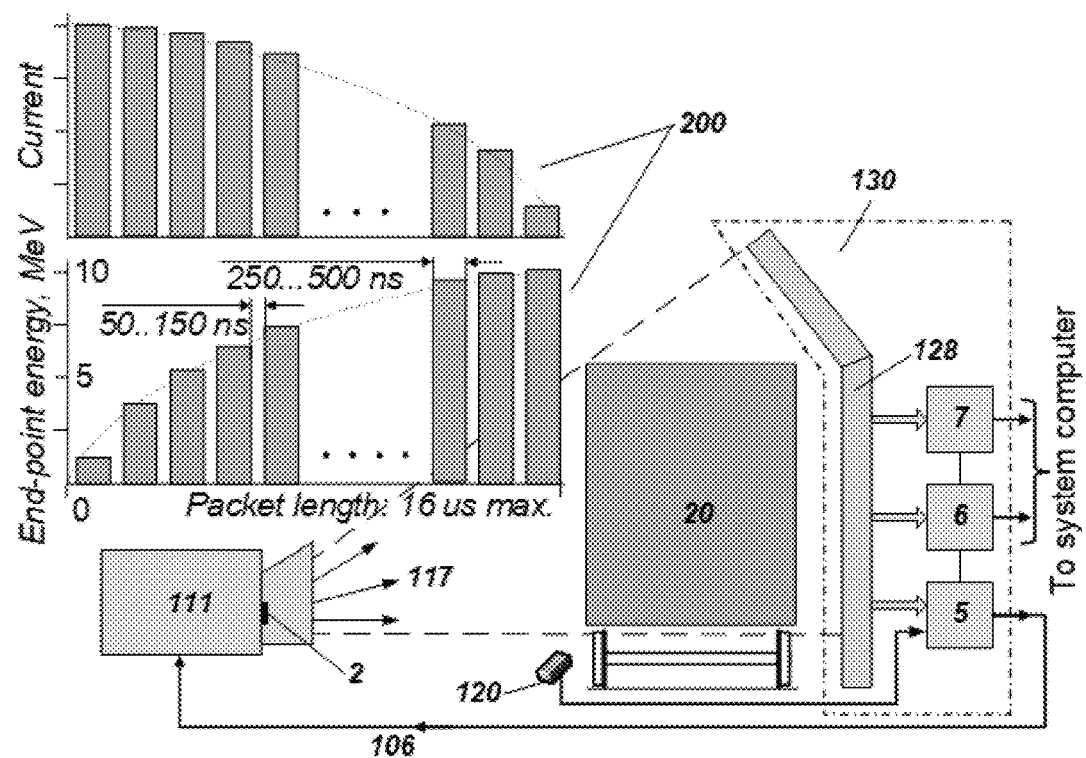
FIG. 3. is a diagram of an example configuration of adaptive transmission X-ray cargo inspection system.

A packet of X-ray pulses 117, FIG. 3, with predetermined energy spectrum profile 200, and with controllable packet duration, is produced that allows multi-energy material discrimination in a single scan line and real-time adjustment of packet duration to adapt to cargo attenuation. In addition, adaptive dynamic adjustment of the operational characteristic of the detector channels increases the effective dynamic range and as a result increases the penetration and range of thicknesses where material discrimination is possible.

The packet of X-rays 117 that have traversed the cargo are detected, in some embodiments, by an array of fast detectors 128, generating a detection signal that allows for a highly efficient and compact detector array. Each pixel of the array is read-out by a Silicon Photomultiplier (SiPM). Generating an X-ray beam consisting of packets of short pulses separated by small time intervals avoids saturation of SiPMs and allows the detectors to reset before the arrival of the next X-ray pulse within the packet. This ability to reset increases the effective dynamic range of detectors and addresses a potential limitation with SiPM recovery time. As the electron energy of the linac is ramped up, the detectors sample the transmitted X-ray flux. The readout signal may reach a saturation point.

In some embodiments, material discrimination is accomplished by controlling the energy ramping within the packet of X-ray pulses. In some embodiments, a dual energy material discrimination is achieved by dividing the readout flux into two separate ranges. This way both high and low energy detector readings belong to the same cargo volume.

In some embodiments, in order to create the packet of X-ray pulses, a radio-frequency (RF) linear accelerator, a linac, is configured to generate a packet of pulses with a programmable set of energies. The packet-mode multi-energy linac switches energies with predetermined energy spectrum profile at a rate of >1 MHz, allowing a controllable packet duration train of pulses of, for example, in some embodiments, ~500 ns duration 200, with energies designed to compensate for the X-ray attenuation of the cargo.

In some embodiments, using detectors capable of resolving X-ray pulses on the sub-microsecond scale, the material discrimination technique is applied within a single packet of short pulses of several hundred nanoseconds, (400 ns for example) separated by about 100 ns gaps (for example) 200. In some embodiments of this scanning technique pulse-by-pulse X-ray energy ramping is utilized during this packet of pulses. The energy of the X-rays produced during the pulse is defined by the energy of the accelerated electrons which is defined by the applied voltage of the accelerator. In some embodiments, a beam loading effect is utilized that will influence energy by adjusting the current or the RF power or both the current and the RF power. An increase of the current of accelerated electrons in the linac pulls down the voltage of the accelerator (and thus energy of the electrons), since the energy of the accelerating RF field, is reduced by the value of the energy transferred to the beam. In complimentary mode, by decreasing the beam current, it is possible to increase the beam energy up to the maximum value defined by the linac design. Alternatively or in conjunction with changes in the current, the input RF power from the RF power source can be changed within the packet of pulses.

Higher RF power increases the accelerating voltage, while lower RF power reduces the accelerating voltage.

In some embodiments, a pre-defined series of steps in electron energy within a single packet is produced by injecting a pre-defined series of steps of electron beam currents, which are controlled by the cathode grid voltage of the electron gun. The packet of X-ray pulses starts from high current/low energy regime and then the beam current is deceased from pulse to pulse, in order to the make the energy ramp up during the packet.

Another aspect of some embodiments is to use feedback 106 from the detection system 130 to control the packet duration of each packet of X-ray pulses, in order to adapt to the object that is being imaged. For example, in some embodiments, after a packet of X-rays are partially absorbed and scattered, and partially transmitted by the object of interest the signals of the X-ray detectors will be analyzed to determine the attenuation of that slice of the object. As the next packet of X-rays will inspect a slice of the object that is nearby to the last packet, it can be assumed that it will have similar attenuation. Therefore, in these embodiments, this analysis is used to determine whether more or fewer high energy pulses should be included in the next packet.

This summary encompasses only some of the illustrative features of the instant invention. A more detailed description is provided below.

DETAILED DESCRIPTION

As used herein and in any appended claims, the following terms shall have the meanings indicated unless the context requires otherwise. The term "Scintillation-Cherenkov detector", SCD, shall signify an X-ray or gamma-ray detector which generate signals due to scintillation process and due to Cherenkov process in response to electromagnetic interaction of secondary electron.

X-Ray Pulse Packet Method.

Currently, high energy X-ray cargo scanning solutions are lacking the ability to scan cargo at high speeds, precluding efficient X-ray scanning of, for example, the railroad cargo for illicit materials such as explosives, drugs and special nuclear materials, SNM with minimal interference with the stream of commerce. The reason for this is the limited X-ray flux available in standard high energy linacs, due to low pulse repetition rate and duty factor. The highest available pulse rates from these sources limit the line frequency of the imaging system and thus the maximum scan speed for a given line resolution. Linear accelerators are available with pulse rates up to 1000 pulses per second (pps). At that rate, an object with a speed of 60 km/h moves 16.7 mm between pulses. The flux is further limited by the fact that material discrimination requires at least two significantly different energies from the linac, typically interlaced one after the other.

While there has been some progress made over the past several years in cargo scanning systems with improved material discrimination, these efforts have seen limited success, mostly due the inability of the current state-of-art detection system to collect data at the X-ray flux rates needed for fast scanning and high cargo penetration.

One aspect of the innovative approach of this patent is to combine fast scintillation, Cherenkov, or Scintillation-Cherenkov detectors, read out by Silicon Photomultipliers (SiPM), with a programmable energy short-pulsed X-ray source, thus allowing energy dispersive data acquisition in each slice at high X-ray fluxes. This approach will vastly expand the ability to scan rail cargo at a system cost comparable to the existing high energy X-ray systems. Because the proposed solution is inherently adaptive to the cargo attenuation, the overall radiation dose to the environment and personnel will be significantly reduced, while the material penetration capabilities will be enhanced. The material discrimination performance, including high-Z material detection, will also be improved over the currently available systems. All these improvements will be applicable to a vast array of object and cargo scanning solutions, not just for rail cargo. While not limiting the application of the instant invention to rail cargo we herein discuss its application to rail cargo as an exemplar application.

Several important new innovations are introduced herein, including but not limited to:

creation of a ramping energy packet of X-ray pulses 200 allows multi-energy material discrimination in a single scan line and real-time adjustment of energies utilized to adapt to cargo attenuation;

the use of a packet of X-ray pulses addresses a known issue with SiPM cumulative saturation due to cell recovery time;

adaptive dynamic adjustment of the responsivity of each SiPM increases effective dynamic range of a SiPM-based CSD, and as a result increases penetration and range of thicknesses where material discrimination possible;

the use of an X-ray detector, utilizing a combination of scintillation and Cherenkov light, reduces the sensitivity to scatter radiation.

An embodiment of the high-speed, adaptive x-ray cargo inspection system is schematically presented in FIG. 3. The packet of X-rays from the linac 117 that has traversed the cargo 20 are detected, in this embodiment, by an array of fast detectors 128, generating a detection signal in high Z crystals that allow for a highly efficient and compact detector array. The X-rays are produced by stopping the electron beam of the linac 116 in the target 2 and generating Bremsstrahlung photons. Each pixel of the array is read-out by a SiPM 704, FIGS. 6 and 7, and signals are processed in the detector electronics 5, 6, 7. Generating an X-ray beam consisting of packets of short pulses separated by small time intervals, avoids SiPMs saturation and allows the SiPMs to reset before the next X-ray pulse within the packet will arrive. This increases the effective dynamic range of detectors with SiPM readout, and addresses a potential limitation with SiPM recovery time. SiPMs offer performance advantages for this type of measurement. The SiPMs are fast photodetectors allowing photon number (energy) and temporal resolution of pulses within a packet. In some embodiments the fast high Z detector materials used are scintillation, Cherenkov, or Scintillation-Cherenkov detectors that have low light yield. SiPMs 704 provide the needed gain and sensitivity to adequately utilize these detector materials. Feedback 106 to the linac 111 from the detector system 130 modifies packet duration. Feedback 106 from speed sensor 129 modifies packet's repetition rate.

Typically, the variation of energy within a train of pulses is an unwanted effect and techniques are used to attempt to compensate for it. Our technical approach is to utilize this effect, indeed to amplify it by using a packet of pulses with a wide range of pulse heights 105. In some embodiments, a rail cargo speed sensor 120 is used to the adjust the linac's packet repetition rate 117 and to define the sampling frequency of the image processing.

Figure 4:
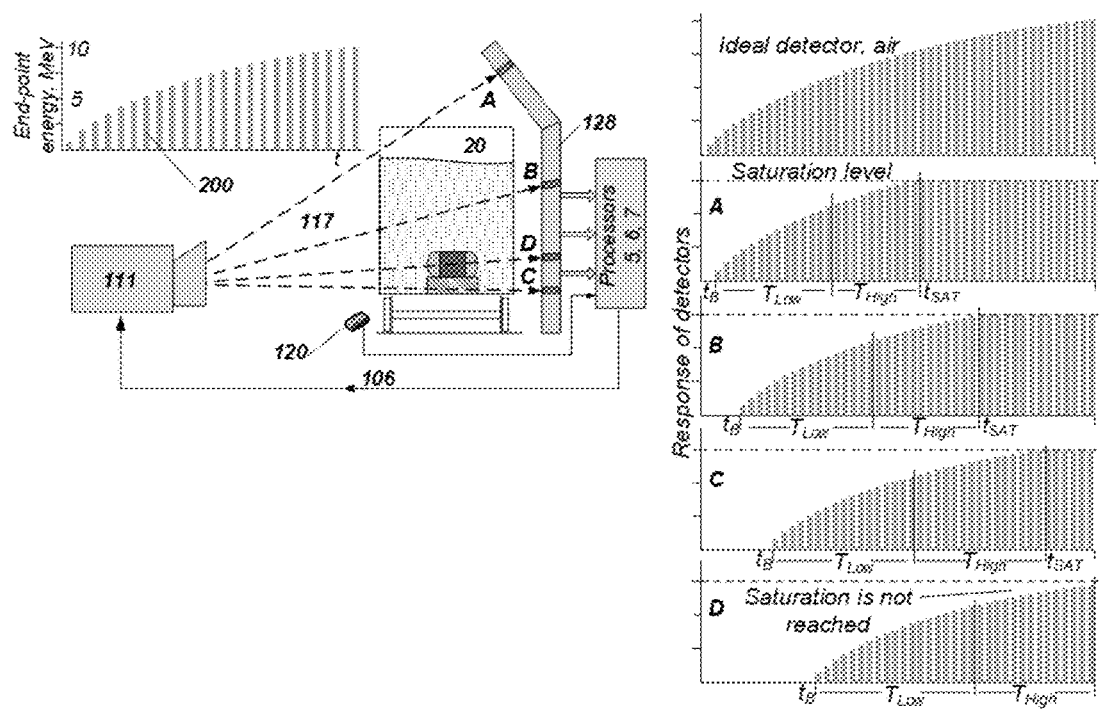
FIG. 4. is a diagram of an example configuration of a cargo x-ray transmission inspection system with detector-linac feedback showing examples of the adaptive ramping energy material discrimination technique within single x-ray slice.

In some embodiments, material discrimination is accomplished by controlling the energy ramping within the packet of X-ray pulses as shown in FIG. 4. As the electron energy of the linac is ramped up 105, the detectors sample the transmitted X-ray flux with different average energy. Due to the nature of the SiPM, the readout signal reaches a saturation point. In some embodiments, the dual energy measurement is achieved by dividing the readout flux into two separate ranges. This way both high and low energy detector readings belong to the same cargo volume. The higher electron to X-ray conversion efficiency of the high energy pulses in the packet will partially compensate for the higher current of the low energy pulses. Thus, there will be sufficient flux at low energy, which is important for material discrimination.

Because the beginning of the detector response and the saturation point ($t_B$ and $t_{SAT}$ in FIG. 4) are both functions of attenuated flux, they can be used as direct measure of the cargo attenuation. Therefore, the duration of each pulse packet can be adjusted based on the feedback from the detectors 106. As such, in some embodiments, the detector array dynamically controls the end-point energy of each packet based on the measured attenuation of the preceding slice.

Figure 5:
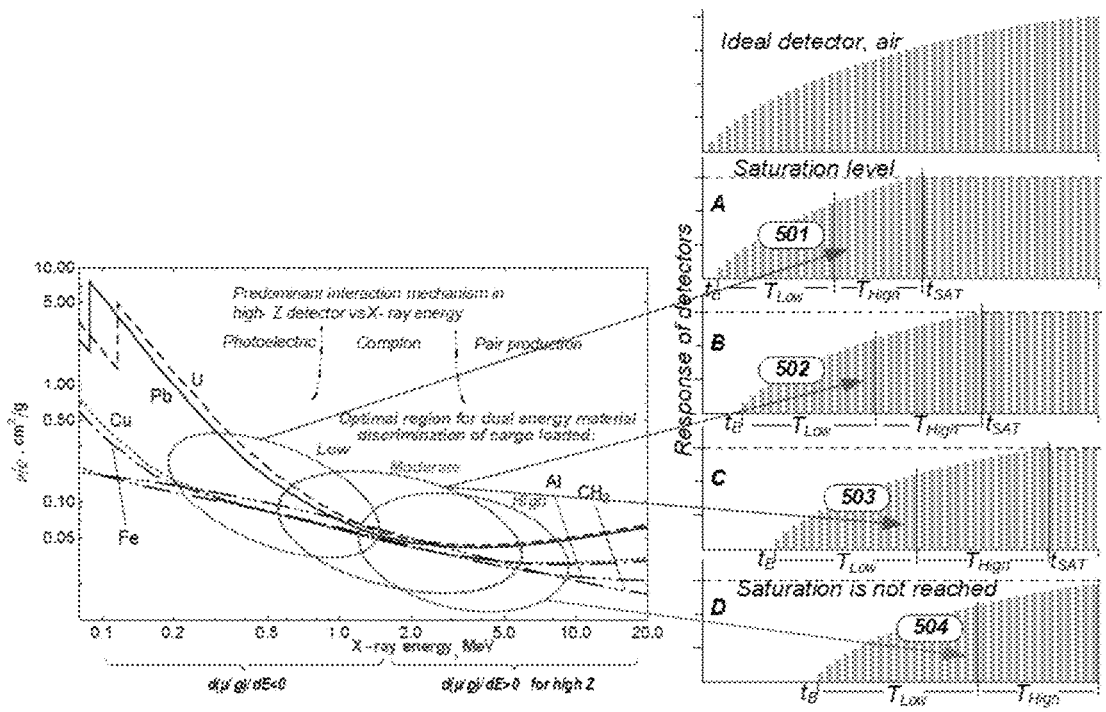
FIG. 5. shows an example of selection of energy windows for material discrimination that depends on cargo attenuation.

The advantages of this type of adaptive scanning technology include higher cargo penetration, better contrast sensitivity and lower external radiation dose. The latter allows reducing the exclusion zone in which the cargo scanner using this technology operates. The ability to quickly analyze X-ray attenuation of rail cargo material provides an added imaging enhancement by extending the penetration range at which it is possible to perform material discrimination. This is illustrated in FIG. 5, where shown mass attenuation coefficients for wide range of materials, from organic to high Z, as a function of X-ray energy, and responses of detector pixels depend on cargo loading 501, 502, 503, 504.

One observes that the attenuation curves for materials exhibit different relative behavior depending on the energy. As such, it is best if the material discrimination procedure is applied differently for distinct cargo thicknesses (light, intermediate and heavy for example). The saturation measurement in each detector can instantaneously provide measure of the total attenuation in cargo on pixel-to-pixel basis. The material discrimination is then performed using the procedures defined for each attenuation range. Such an approach allows performing material discrimination at cargo thicknesses not achievable with the conventional interlaced dual energy linac.

While the most common X-ray scanning systems with material discrimination use interlaced dual energy linacs, they have fundamental limitations when used for high speed rail cargo scanning. These limitations are well known and include among others: significant spatial separation between volume interrogated by high and low energy beams resulting in incorrect material discrimination of heterogeneous cargo incomplete imaging of the fast moving object under inspection due to limied X-ray pulse repetition rate; and limited penetration.

Accelerator

In order to create the packet of X-ray pulses, an RF linear accelerator 111 is configured to generate a packet of pulses with a predetermined energy spectrum profile but allowing for a controllable packet duration. Unlike conventional dual-energy linacs, which switch energy at a rate of at most 1 kHz, the packet-mode multi-energy linac switches energies at a rate of >1 MHz, allowing a packet of pulses of, for example, in some embodiments, ~500 ns duration is generated, with energies designed to match the X-ray attenuation of the cargo.

Commonly bremsstrahlung generated X-rays are used to perform radiography of cargo containers and other objects. Information (such as, but not limited, to mass absorption coefficient, effective atomic number $Z_{eff}$ and electron density) with respect to the material composition of the contents of objects may be obtained on the basis of the interaction of X-rays with the material, and, more particularly, by illuminating the material with X-ray beams having energy spectra with more than one distinct energy endpoint (peak energy). Dual energy methods of material discrimination are widely used in such systems. The bremsstrahlung spectrum of X-rays produced at each electron beam energy, which is known, is used along with known nuclear physics relationships of X-ray absorption dependent on the atomic number (Z) (or atomic numbers for multiple elements) of the material being imaged.

Conventional, linac-based cargo inspection systems with material discrimination provide X-ray pulses with two energies (for examples, 4 and 6 MeV, or 6 and 9 MeV) that are alternated from pulse to pulse with repetition rate up to 400 Hz. While this technique is well developed, it has three major limitations. First of all, since each pulse is typically separated by >1 ms, fast moving cargo will not provide overlap of the two energies on the same slice of material, so the material discrimination technique will not deliver accurate information about the Z characteristic of the slice. Second, detector element sizes, together with object motion effects result in very little actual cargo being sampled (less than 25%) at high speeds (under sampling). Third, this technique has fixed two energy levels which are optimal for material discrimination in a limited region of object thicknesses. Therefore it does not allow adaptation to the X-ray attenuation of the specific slice of cargo. This causes difficulties with material discrimination for regions of low density and high density, and adds to the environmental radiation dose rate of the system, since most of the time the higher energy is not necessary to penetrate the cargo and provide material discrimination.

Several approaches have been proposed in order to solve these problems, however none of them solve all the problems the conventional dual-energy technique. They still use the fixed dual energy pulse by pulse approach, where the pulses are separated by a significant time gaps of a millisecond scale. Even if the pulse length is controlled to reduce the radiation dose acquired by the inspected object, it is not enough to effectively adapt the X-ray energy regime to the wide range of cargo load. The use of several parallel detector arrays or even the multi-beam approach to improve the sampling rate make the inspection system significantly more expensive.

Figure 11:
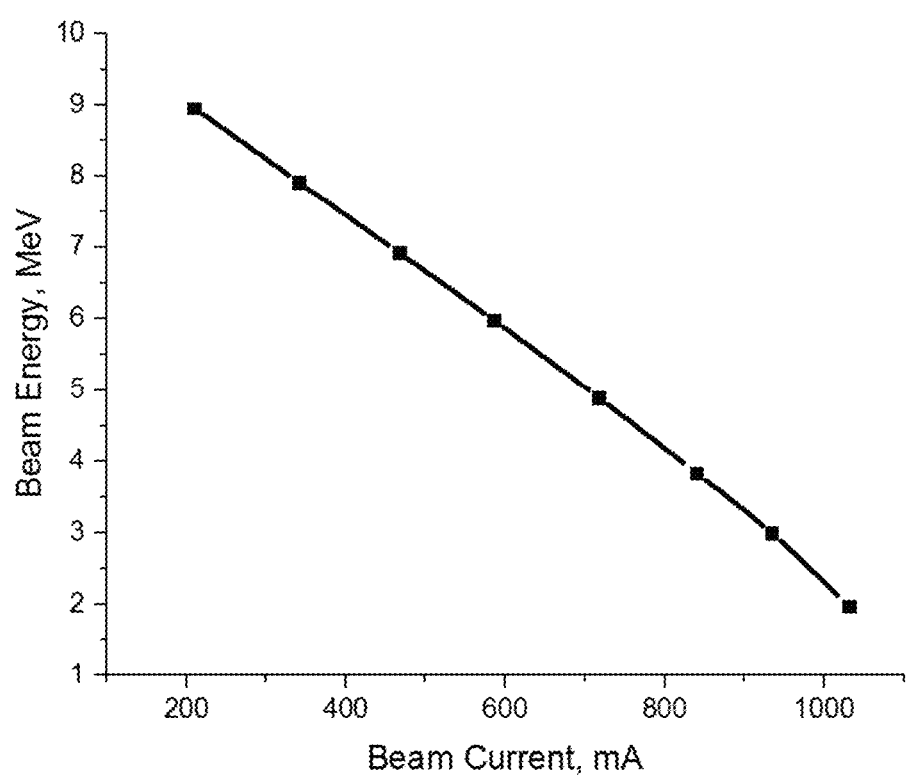
FIG. 11. is an example of a loading curve for a linac showing the dependence of x-ray energy as a function of accelerated current.

In some embodiments, using detectors capable of resolving X-ray pulses on the sub-microsecond scale, the material discrimination technique is applied within a single packet of short pulses (several hundred nanoseconds, 400 ns for example) separated by about 100 ns gaps. In some embodiments of this scanning technique pulse-by-pulse X-ray energy ramping is utilized during this packet of pulses. The energy of the X-rays produced during the pulse is defined by the energy of the accelerated electrons, which can be controlled, in some embodiments, by utilizing the beam loading effect. The increase of the current of accelerated electrons in the linac pulls down the voltage of the accelerator (and thus energy of the electrons), since the energy of the wave, is reduced by the by the value of the energy transferred to the beam. In complimentary mode, by decreasing the beam current, it is possible to increase the beam energy up to the maximum value defined by the linac design. The relationship between beam energy and the current (so called loading curve) is defined by the linac design and the power source. The total energy balance of the accelerator can be described by the formula:

$$P_{RF}=P_{beam}+P_{losses}+P_{load}=UI+U^2/R+P_{load},$$

Where $P_{RF}$ is the RF power delivered by the RF power source (e.g. magnetron, klystron), $P_{bea}$ is the power that the beam acquired from the linac, $P_{losses}$ is the heat dissipation power, and $P_{load}$ is the unused part of the power, U is the voltage gain of the beam, I is the accelerated beam current, and R characterizes the Eddy current wall losses inside a linac. The typical loading curve in some embodiments, shown in FIG. 11, is defined by the specifics of the linac design and cannot be changed during the linac operation.

In some embodiments a pre-defined series of steps in electron energy within a single packet is produced by injecting a pre-defined series of steps of electron beam currents, which are controlled by the cathode grid voltage of the electron gun. The packet of X-ray pulses starts from high current/low energy regime and then the beam current is deceased from pulse to pulse, in order to the make the energy ramp up during the packet.

By utilizing the energy ramping up during the packet of X-ray pulses, the material discrimination can be performed on a much faster timescale (the scale of this packet of pulses), which is especially important for high speed cargo inspection. Another advantage is the adaptability of the duration of the packet of pulses. Depending on the X-ray attenuation of the inspected cargo slice, the X-ray packet length can be reduced if it is determined that the cargo has been fully penetrated by the X-rays. In this case, the end point energy of the packet will be proportional to the packet duration and lower than the maximal achievable energy (for example, 6 MeV instead of 9 MeV). This shortens the X-ray exposure time and allows reduction of the environmental dose rate and reduced footprint of the exclusion area.

Figure 9:
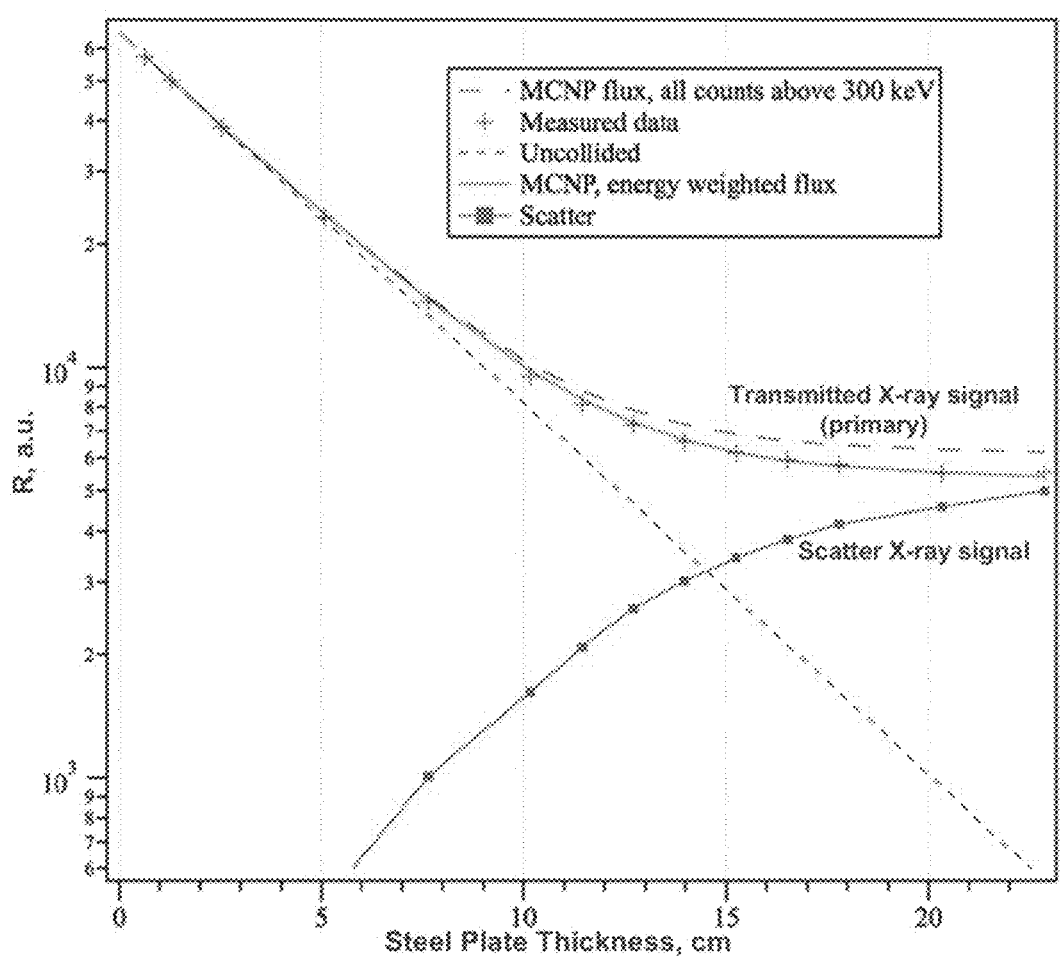
FIG. 9. is a plot of measured transmitted x-ray signal and scattered x-ray signal as a function of thickness of attenuating steel plate [adopted from E. Miller, et al. Scatter in cargo radiography. Applied Radiation and Isotopes, 69 (2011) 594-603.]
Figure 12:
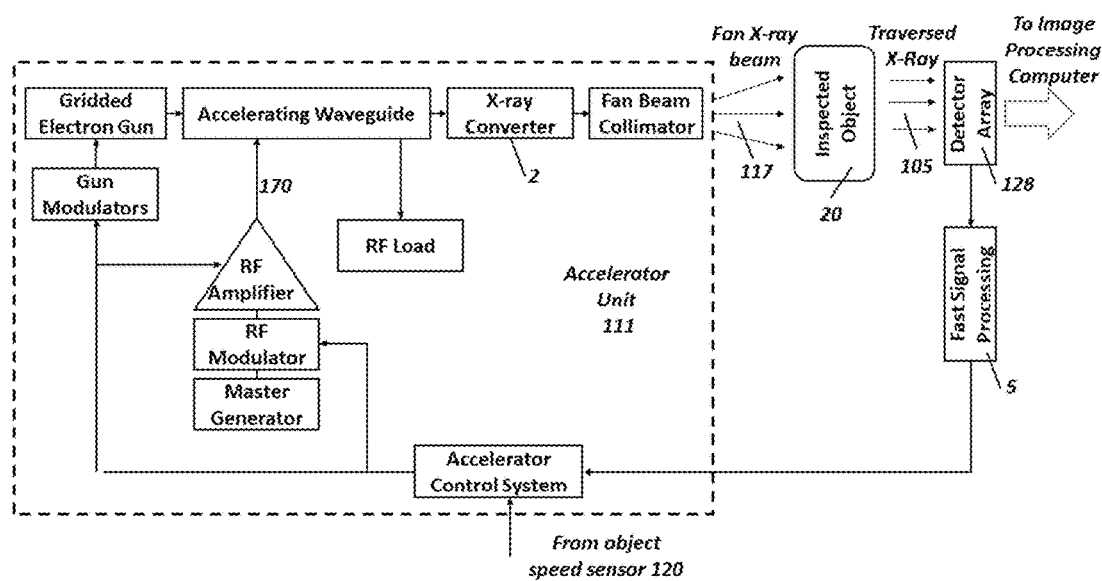
FIG. 12 is a diagram of an example of the x-ray generator layout and control method based on a traveling wave linac approach.

FIG. 12 demonstrates the block scheme of some embodiments of the X-ray generation unit 111. The electron beam is generated from the electron gun and injected into the linear accelerator, fed by RF power, where the electron's energy is increased, depending on the injected current and RF power 170. The unused RF power is dumped into the RF load. Since traveling wave regime is used, the fields in accelerating waveguide cannot provide radial beam stability and electromagnetic solenoid is required. The accelerated beam then hits the conversion target and produces X-Ray radiation, which then passes through a collimator 114 to shape the X-ray beam. The X-ray pulse 117 then passes through the inspected object 20 where it is partially absorbed and scattered, and finally reaches the detector array. The relationship between scatter and transmitted x-rays is a function of the amount of material in the object 20 FIG. 9. Based on the information from all detector array channels, which calculates the X-ray attenuation in the latest slice of the scan, the fast processor for linac control 5 makes the decision on whether the next packet of pulses should be shorter or longer (i.e. controls the end point energy of the packet pulse). The control system then sets the voltage to the cathode grid that defines the value of the current injected to the accelerator, and therefore, the energy of the X-Ray. The required speed of the pulse modulation is ensured by using special high speed electronic circuits.

Figure 13:
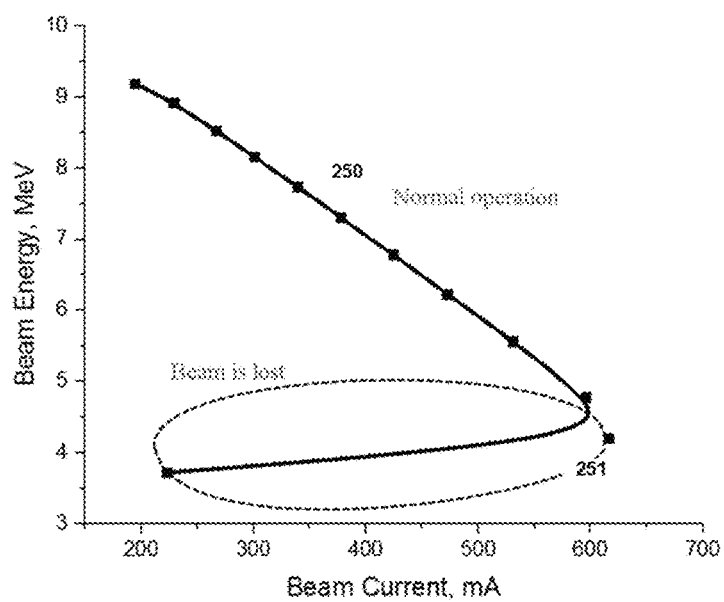
FIG. 13 Is a plot of an example of loading curve of the single-section standing wave linac.

In some embodiments a travelling wave S-band accelerator is utilized that is capable of producing ~1.5 MW (peak) electron beam with the ability to change the energy of electrons during the RF pulse from 2 to 9 MeV. The lower energy boundary is significantly improved compared to the conventional single-section standing wave linacs (usually 4-5 MeV). FIG. 13 demonstrates the typical loading curve 250 of such a (conventional) linac. After reaching the critical value of the injected current 251, the linac bunching and focusing efficiency drops abruptly, resulting in significant reduction of the accelerated current that reaches the conversion target (eventually, to almost 0 amps). This problem has been solved by switching the operation regime from standing to traveling wave, where the field distribution in the bunching section is less sensitive to the beam loading effect, as well as by proper design of the bunching section that effectively groups the electron beam into small bunches. This technique is used in this embodiment to control energy and current within a single packet over a wide range.

In some embodiments the electron beam current is controlled by gating emission with electrodes in between the cathode and anode. The electrodes modify the voltage on the surface of the cathode, thus allowing control of output current according to the Child law. The most common type of electrode is a grid placed very close to the cathode (~100 μm), so that a small voltage on the grid with respect to the cathode can produce a large change in electric field and thus emitted current. Other types of modulating anodes can also be used for the same purpose. Thus modulating the voltage on these intermediate electrodes results in modulation of the electron beam current. Typical techniques for modulating the voltage on these electrodes to produce short pulses of varying heights include linear amplifiers or inductive adders. While such current control techniques are commonly used on linacs, they are typically much slower than what is envisioned to be used in this approach. That is, typically the intermediate electrode voltages are changed at the fastest in between sequential pulses (i.e. <1 kHz). Some embodiments apply these electrode modulation pulses at a much faster rate, >1 MHz, in order to achieve current and energy variation within a single packet.

One skilled in the art of linac design may devise additional embodiments of the linac design changed in regard of the particular requirements of the instant inspection system (energy range, intensity, dimension etc.). Different embodiments may include a different frequency band, different acceleration scheme (standing wave, hybrid etc.), or even a different acceleration method (i.e. circular accelerator) all of which are included in the scope of the instant system.

In some embodiments, the control of the pulses is accomplished by exploiting the beam-loading effect in a packet of pulses. A packet of electron pulses with distinct, programmable pulse currents are injected into the accelerator from an electron gun. The current of each electron pulse from the electron gun can be controlled with a variety of methods. The most common method currently used is by setting the voltage of a grid structure placed just a fraction of a millimeter away from the cathode surface. The grid voltage is then adjusted with respect to the cathode potential in order to either cut off emission from the cathode (by effectively canceling the cathode-anode potential) or to allow emission to varying degrees. As the grid voltage required for current control is relatively low (~100 V), it can be varied rapidly. In one embodiment a packet of 400 ns pulses generated by the Tektronix AFG2021 arbitrary function generator can be amplified to drive the grid of the electron gun and produce pulses with distinct currents.

In some embodiments, the packet of electron pulses follow a pattern of decreasing current pulse heights, as shown in FIG. 11. The accelerating voltage of an RF linear accelerator follows the following relationship, which describes the effect commonly known as beam loading:

$$V = F(P_0 r_s l)^{1/2} - G r_s l i$$

where $P_0$ is the input RF power, $r_s = E^2/2\tau P_0$ is the Linac shunt impedance, i is the beam current, l the effective length of the accelerating cavity, E is a peak field gradient on-axis, and F and G are constants dependent on the geometry of the accelerator. One can see that higher electron beam current results in a lower accelerating voltage. Where the current of each pulse decreases sequentially, the first pulses will be lower energy than the later pulses.

Another source of control over the energy of the pulses is the input RF power, $P_0$. This can also be varied with time, for example by using a klystron amplifier as the high-power RF source. The RF output pulse can have time variations by either modulating the input RF power to the klystron or by modulating the driving voltage. In this embodiment, the power can have a slope to it, either downward or upward, which allows one to increase the current at a given energy, as determined by the needs for achieving sufficient signal strength in the X-ray detectors.

We note that this is a rather limited explanation of the beam-loading effect, and that there are other complications to consider, such as transient effects and longitudinal beam dynamics. However, this effect has been shown to be successful in conventional interlaced linacs for cargo inspection, although with much slower switching of pulses (time between different energy pulses on the order of several millisecond, vs. approximately 100 ns in our approach). These concepts are extended to produce a packet of pulses with a wide range of energies, for example, in some embodiments, from 2 to 9 MeV.

Once the electron pulses are injected and accelerated, they are then collided with an X-ray converter. The X-ray converter 70 consists of one or more layers of one or more types of metals. When high-energy electrons pass through the converter materials, they produce X-rays through the bremsstrahlung process. In the prior art X-ray converters are designed for a limited range of energies (e.g. 6-9 MeV). In some embodiments of the instant invention, the X-ray converter 70 is designed to provide good X-ray conversion efficiency for a much wider range of energies, for example from 1 to 9 MeV, while at the same time stopping substantially all the high-energy electrons in the converter. If the high energy electrons are transmitted through the converter, they will produce X-rays in other locations in the inspection system or in the object being inspected, and will reduce the performance of the inspection system. Therefore, the density and thickness of each layer is chosen to maximize the efficiency of X-ray conversion across the desire range of energy for the X-ray pulses, while stopping substantially all the electrons in the converter.

In some embodiments the pulses will be separated by approximately 100 ns time interval, which allows the SiPM 704 to reset. The generation of trains of fast, ~ns pulses is a well-established technique in accelerators, having been performed at SLAC in the 1960's and at many other facilities in the decades since. These pulse trains are typically created either with modulation of the electron gun grid voltage or by using a laser on a photocathode.

In the past, this variation of energy between pulses has been considered an unwanted effect, and techniques were applied in order to minimize it. One aspect of the embodiment described here is to utilize the pulse current and RF power to make a programmed set of pulses with wide energy variation, which is beneficial for certain applications such as X-ray cargo inspection.

An aspect of this embodiment is to use feedback 106 from the detection system 130 to control 120 the characteristics of each packet of X-ray pulses 117 (number of pulses, energy and current of the pulses), in order to adapt to the object that is being imaged. For example, in some embodiments, after a packet of X-rays the signals of the X-ray detectors will be analyzed to determine the attenuation of that slice of the object. As the next packet of X-rays will inspect a slice of the object that is nearby to the last packet, it can be assumed that it will have similar attenuation. Therefore, in this embodiment, this analysis is used to determine whether more or fewer high energy pulses should be included in the next packet.

Scintillation-Cherenkov Detector with Rejection of Scatter X-Ray (Directional SCD)

A typical scintillator detector consists of a volume of a light-transparent scintillation medium 707 optically coupled to one or more photodetectors 704, each, usually a photomultiplier tube or a solid state photodetector. If the energy of the X-ray is small, the photodetector signal which arises from the scintillation mechanism is typically proportional to the energy of the electron(s) generated in the medium by the photoelectric and/or Compton effect. Conversion of the energy of the incident X-ray to visible light may occur through multiple scattering processes, with a significant fraction (the conversion efficiency) of the energy ultimately converted and detected by one or more photodetectors. Cherenkov radiation occurs when the recoil electrons have energy above the Cherenkov threshold, which is to say that the electrons pass through a detector medium (any optically transparent medium, including scintillators) faster than light travels in that medium. For sufficiently energetic X-rays the energy of the generated electrons can achieve the Cherenkov threshold condition. In practice, the effective threshold energy can be between 1 and 3 MeV, dependent on the detector configuration and the properties of the medium.

Cherenkov radiation is the electromagnetic "shock-wave" of light generated by a relativistic charged particle travelling beyond the speed of light in the medium. The photons of Cherenkov radiation have a continuous spectrum from the ultraviolet to the infrared. The duration of Cherenkov radiation in detectors is very short; typically a few hundred picoseconds. In contrast with Cherenkov radiation, the scintillation mechanism is a process of light generation by a moving charged particle exciting the medium. Typical scintillators generate light in the visible region. The duration of the light is dominated by the exponential decay of the scintillation with decay times from tens to thousands of nanoseconds.

In accordance with embodiments of the present invention, both the scintillation and the Cerenkov light produced by an X-ray may be measured independently in the same medium. While the scintillation light is proportional to the total energy deposited by the X-ray-generated electrons and positrons, Cherenkov light is produced only by electrons and positrons with energy above the Cherenkov threshold.

In some embodiments the detector utilizes both the scintillation light and the Cherenkov radiation produced by the X-ray in the same scintillation medium. The difference in the mechanisms of light generation between scintillation and Cherenkov radiation results in the duration of the Cherenkov light pulse being at least one order of magnitude shorter than the duration of scintillation light.

Figure 6:
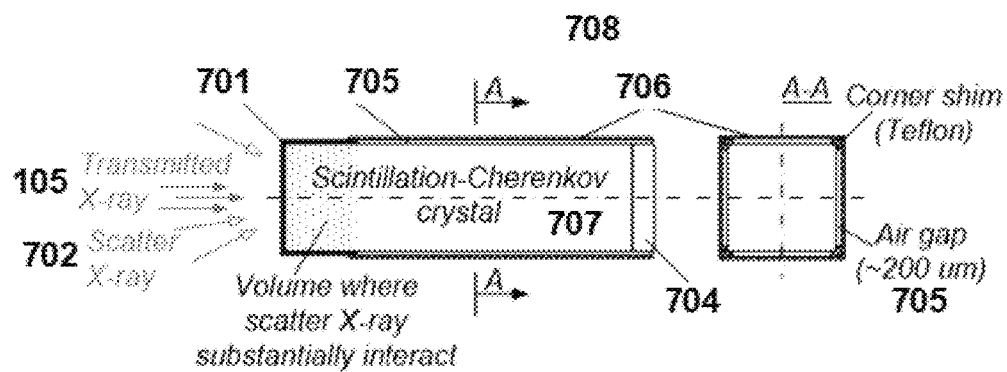
FIG. 6. is a diagram of an example of the design of a Scintillation-Cherenkov detector with scatter rejection.
Figure 7:
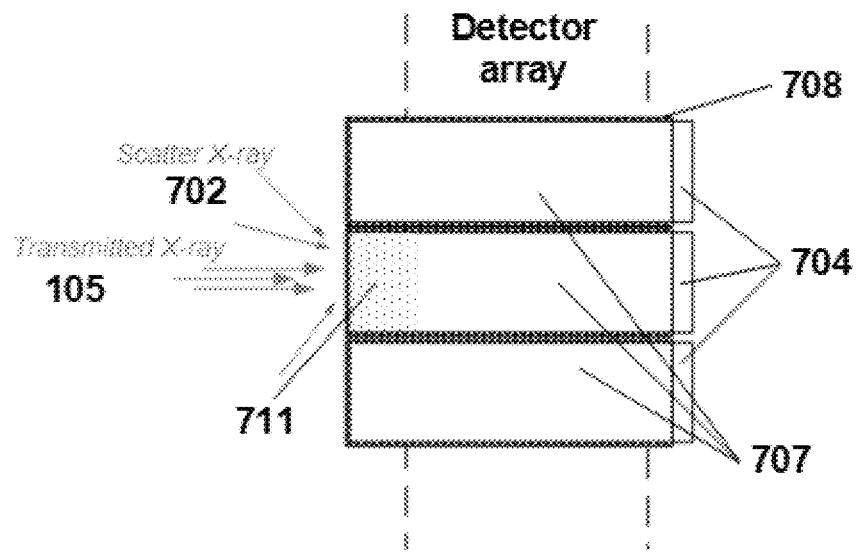
FIG. 7. is a diagram showing an example of scatter radiation interacting substantially within the front part of a detector crystal.

In accordance with some embodiments of the present invention, a detector 708 is provided for detecting and characterizing high energy penetrating radiation, FIG. 6. The detector has a detecting medium 707 for generating kinetic charged particles and, in response thereto, emitting electromagnetic radiation. Additionally, the detector has at least one photodetector 704 for detecting electromagnetic radiation emitted by the detecting medium through a Cherenkov radiation process and through a scintillation process, and a signal conditioning module, coupled to the at least one photodetector, for discriminating detector signal components due respectively to Cherenkov and scintillation processes.

In some embodiments the detector may have a signal conditioning module of a kind that discriminates between components due respectively to Cherenkov and scintillation processes on the basis of spectral features of the scintillation process and the Cherenkov radiation process. Alternatively, the signal conditioning module may be of a kind that discriminates between components due respectively to Cherenkov and scintillation processes on the basis of temporal features of the scintillation process and the Cherenkov radiation process.

In some embodiments the signal conditioning module may distinguish between a high temporal frequency component associated with the Cherenkov component of the detector signal and a low temporal frequency component associated with the scintillation component of the detector signal. It may extrapolate, in response to a pulse of radiation, a temporal tail of the detector signal that persists after the pulse, to derive a scintillation component of the detector signal during the pulse. It may subtract a scintillation component of the detector signal during the pulse of radiation from a total measured detector signal during the pulse to derive a Cherenkov component of the detector signal during the pulse.

In some embodiments the detector may have more than one photodetector, such as a first photodetector for detecting electromagnetic radiation emitted by the detecting medium through a Cherenkov radiation process and a separate, second photodetector for detecting electromagnetic radiation emitted by the detecting medium through a scintillation process. There may be a first photodetector signal conditioning module for receiving a first detector signal associated with the first photodetector and a second photodetector signal conditioning module for receiving a second detector signal associated with the second photodetector. The first signal conditioning module includes a photon-counting electronics module, and the second signal conditioning module includes a current-integrating electronics module. The first signal conditioning module may also include a gated amplifier for amplifying a signal during a specified duration of time in synchrony with emission of penetrating radiation by the source.

The photons with energy above the Cherenkov threshold are most likely photons that have passed through the inspected object without interaction, i.e. they are not scattered photons, since scattered photons, having lost energy on scattering, are more likely to have been scattered to energies below the Cherenkov threshold. The ratio of the signals from both channels is a measure of the high energy fraction of the X-ray spectrum which penetrates the object 20. The technique can discriminate against low energy photons, which consist at least in part of scattered radiation 702, and thus eliminate their contribution to the image so that the contrast is increased.

Figure 8:
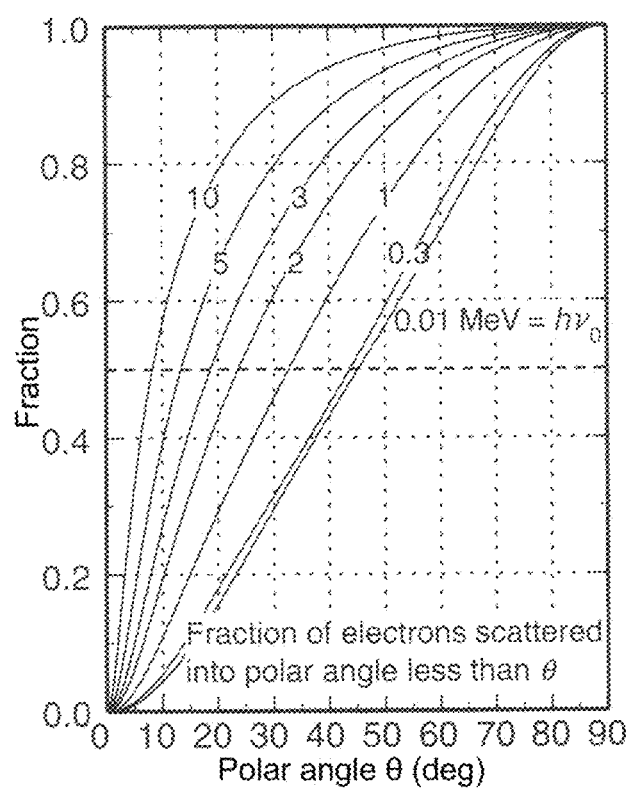
FIG. 8. is a chart showing the cumulative fraction of electrons scattered into a polar angle [adopted from N. Carrion. An introduction to the Passage of Energetic Particles through Matter. Taylor & Francis, 2007. 362p]
Figure 17:
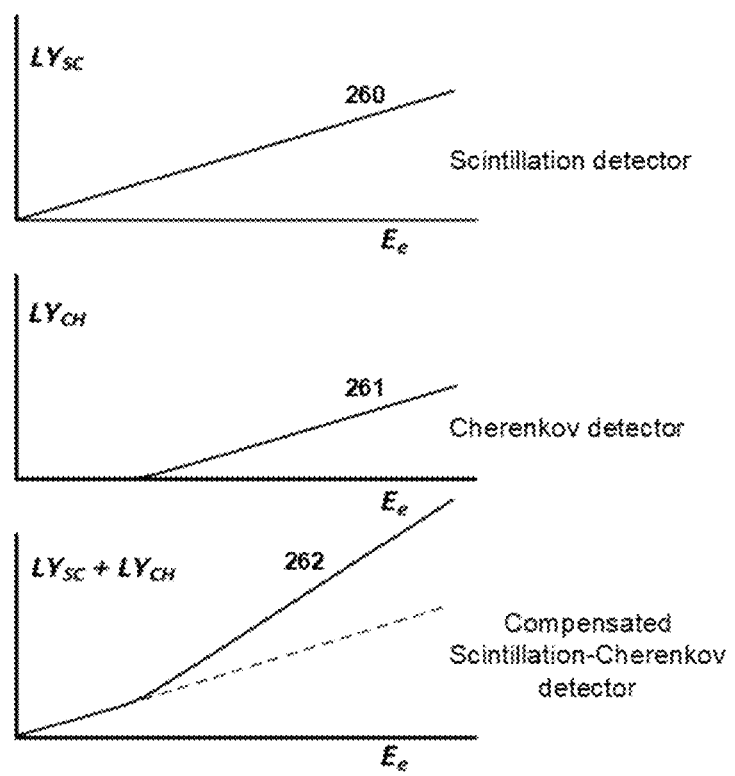
FIG. 17 is a plot of light response for a representative Scintillation detector, a representative Cherenkov detector and a Compensated Scintillation-Cherenkov detector.

In some embodiments the mechanism for rejection of scatter radiation in Scintillation-Cherenkov detector is based on two things. First, in one embodiment, the active material for the detector 707 is a compensated Scintillation-Cherenkov crystal. In such detector crystals, the Cherenkov light yield 261 produced by a minimum ionizing particle is about equal to scintillation light yield FIG. 17. Second, the design of detector pixel, FIG. 6: light absorption cap 701 in the beginning of crystal; and an air gap 705 between the side surfaces of the crystal and a light reflector 706 around crystal. With this design, the light generated by scatter radiation 702—mostly in the portion of the crystal that is proximal to the radiation source 711, FIG. 7, will be effectively absorbed by a light absorbing cap 701 (e.g. an optically black material) and will not contaminate the Cherenkov light generated by transmitted radiation 105, which is directed along the main crystal axis. Only the Cherenkov fraction of light will be directed along the main axis, FIG. 8. Scintillation light will have 4-pi emission distribution, but more scintillation light produced by interactions deeper into the detector medium 707 will reach the photodetectors 704 on the distal end of the detector medium than light produced on the proximal end of the detector medium, which is absorbed to a greater extent by the light absorbing cap 701. The angle of incidence and higher energy for non-scattered x-rays 105 will favor deeper interactions thus producing a higher signal than for incident scattered x-rays 702.

Figure 10:
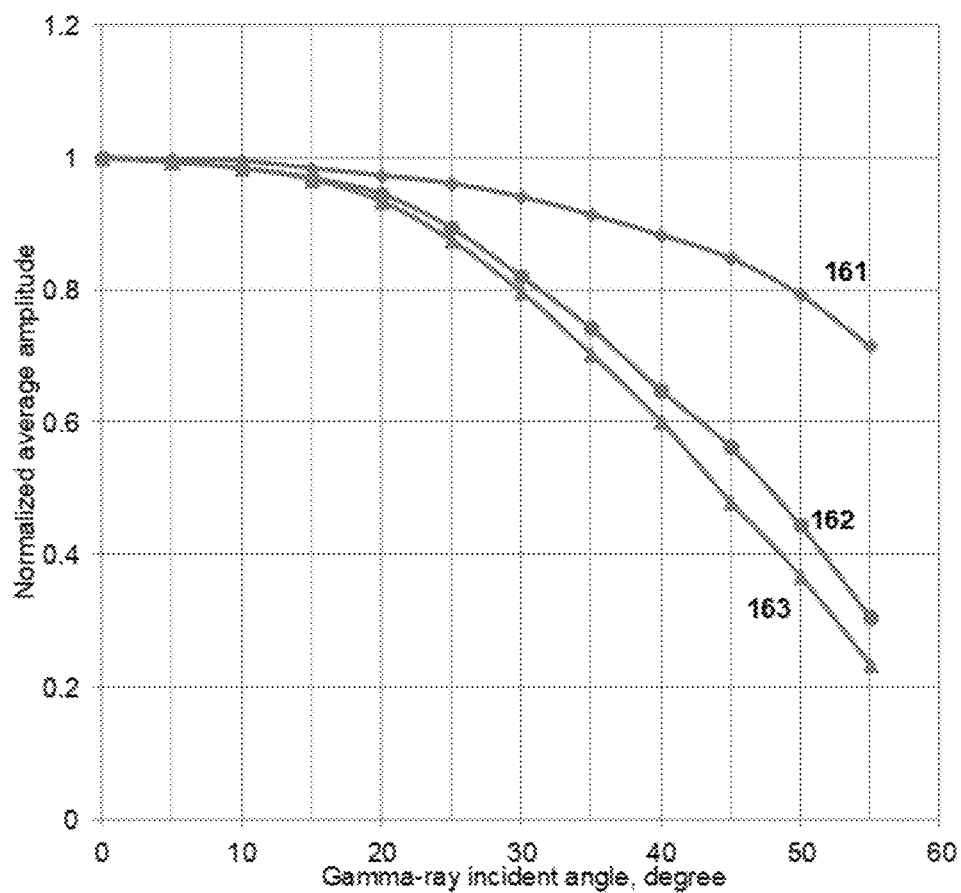
FIG. 10. is an example of a plot of the normalized average amplitude versus the angle of incidence of incoming photons for two detector configurations.

Examples of the effect of utilizing an air gap in this detector design is shown in FIG. 10. Normalized average amplitude is show as a function of incident angle for a Teflon wrapping detector for 2.61 MeV incident energy photons 161. Normalized average amplitude is show as a function of incident angle for the detector with air gap design for 2.61 MeV incident energy photons 162. Normalized average amplitude is show as a function of incident angle for the air gap design for 1.33 MeV incident energy photons 163.

Typically a predominantly scintillation (non-Cherenkov) detector produces an approximately linear output of detectable light as a function of the input energy quanta 260. Likewise typically a predominantly Cherenkov detector produces an approximately linear output of detectable light as a function of the input energy quanta 261. A non-linear light response is generated from a detector material that has similar light response for both scintillation and for Cherenkov radiation 262 (referred to as a Compensated Scintillation-Cherenkov Detector). In such a detector, the relationship between deposited energy and emitted light can be non-linear so that proportionally more energy is converted into detectable light as the energy increases beyond the point where Cherenkov radiation initiates 262. This increase in light generation can be used to partially compensate for decreased photon flux with increasing linac energy.

The Scintillation-Cherenkov detector is able to use signals produced from both the scintillation process and the Cherenkov process. Detector signals that are derived separately from scintillation and Cherenkov detection processes are used to enhance imaging over the entire range of attenuation that is expected in cargo. For example, scintillation may be used dominantly in lower attenuation of regions of the cargo, where scatter is not a limiting factor. In high-attenuation regions, where penetration is essential and sensitivity is limited by scatter, a Cherenkov signal may be used to preferentially filter out the scatter. In some embodiments the combination of multi-energy inspection and joint scintillation and Cherenkov detection advantageously sorts materials by effective atomic number.

SiPM-Based Read-Out with Adaptive Responsivity

SiPMs are photon detectors that are mostly associated with multi-pixel Geiger mode avalanche photodiodes (APDs) with built-in negative feedback elements. Strong negative feedback applied to the Geiger avalanche breakdown enables reliable quenching of avalanche breakdown and near ideal single electron multiplication with very high gain ($10^4$-$10^6$) and ultra-low excess noise factor (excess noise factor 1.01-1.05). The multi-pixel architecture provides capability for multi-photon pulse detection with superior photon number resolution starting from single photons.

SiPMs are widely recognized to be competitive with conventional vacuum photomultiplier tubes (PMT) and avalanche photodiodes (APD) in various low light level applications due to their unique photon number resolution at room temperature, exceptional single photon time resolution, low operating voltages, compactness, and insensitivity to magnetic fields. Detection of short weak light pulses of nanosecond time scale appear to be the best suited for SiPM applications because for these signals most of the SiPM drawbacks have rather limited effect on the amplitude and time resolution of the signal. For these reasons, the most popular applications of SiPM technology are a low-light short-decay scintillation and Cherenkov light detection.

In X-ray cargo inspection systems, the intensities of scintillation and Cherenkov signals in detectors can vary by as much as 1:100,000 due to highly variable X-ray absorption inside the cargo. This application is rather challenging for photon detectors of any kind because in order to reconstruct an absorption profile inside a cargo under test it requires superior energy and temporal resolution of high dynamic range light signals starting from very low number of photons.

Figure 14:
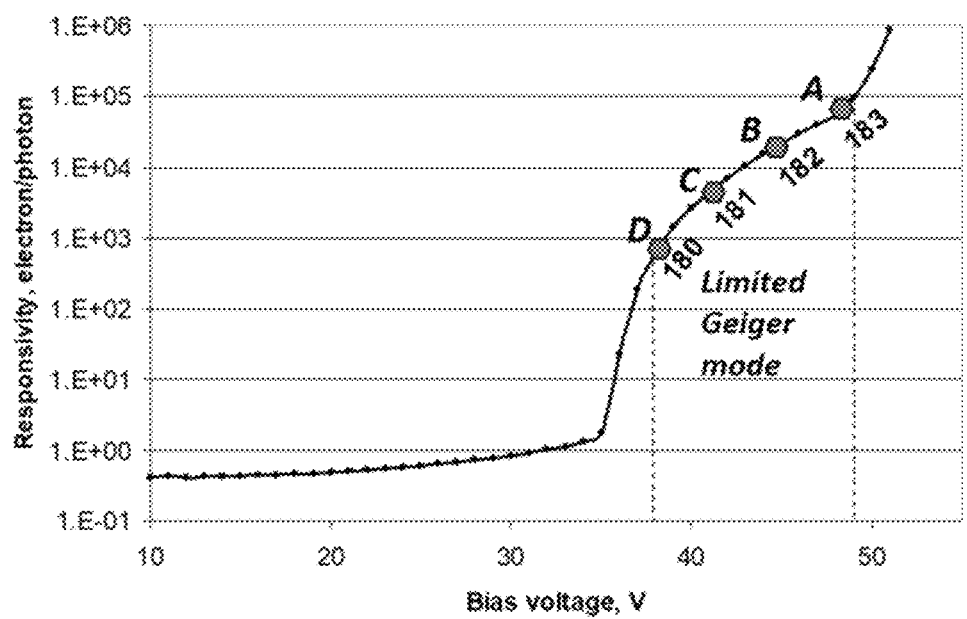
FIG. 14 is a plot of an example of dependence of SiPM responsivity to bias voltage over a wide operating range.

FIG. 14 is a plot presenting the dependence of typical SiPM responsivity on applied bias voltage. The conventional operating mode of SiPM is a limited Geiger mode which provides efficient quenching of an avalanche breakdown process. In this mode the SiPM gain is linearly proportional to the over-breakdown voltage (overvoltage) 183, 182, 181, 180, and the photon detection efficiency (PDE) is a sub-linear function of the overvoltage.

However, a SiPM operating in a limited Geiger mode is a non-linear photodetector. SiPM output response on large incident signals approaches saturation due to the limited number of pixels and finite pixel recovery time. In case of a long light pulse detection (where the light pulse duration is much greater than the pixel recovery time), the SiPM response non-linearity could be approximately described by a non-paralyzing dead time model [S. Vinogradov et al., "Efficiency of Solid State Photomultipliers in Photon Number Resolution", IEEE Trans. Nucl. Sci., vol. 58, no.1, pp. 9-16, 2011, which is incorporated herein by reference].

Figure 15:
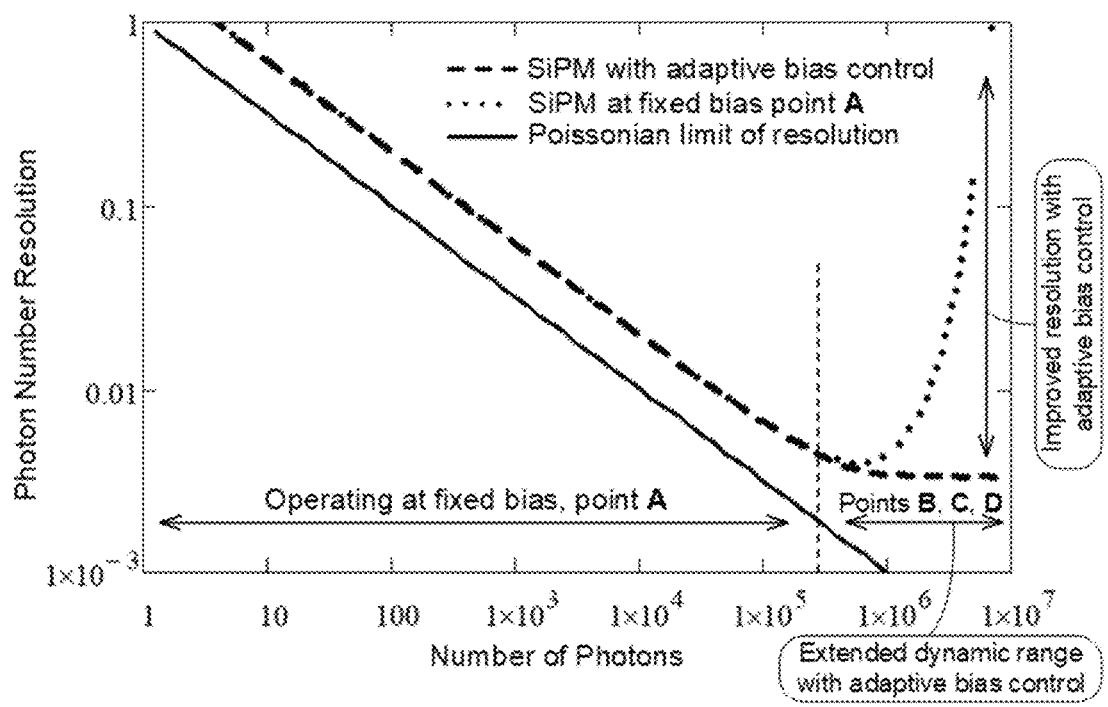
FIG. 15 is a plot showing an example of a photon number resolution of a SiPM operating in a fixed voltage and adaptive regimes.

If an output response (calibration) function is known and provides relevant correspondence with the experimental results, it is possible to reconstruct incident number of photons for a known output response using a known inverse fit function. Regretfully, this procedure becomes more and more inaccurate i.e. signal resolution becomes worse (see FIG. 15, curve "SiPM at fixed bias point A") as the output becomes more and more saturated because of specific excess noise of saturation process due to the dramatic increase of losses in the number of detected photons. This means that any contrast details in a saturated image would not be resolved.

Figure 16:
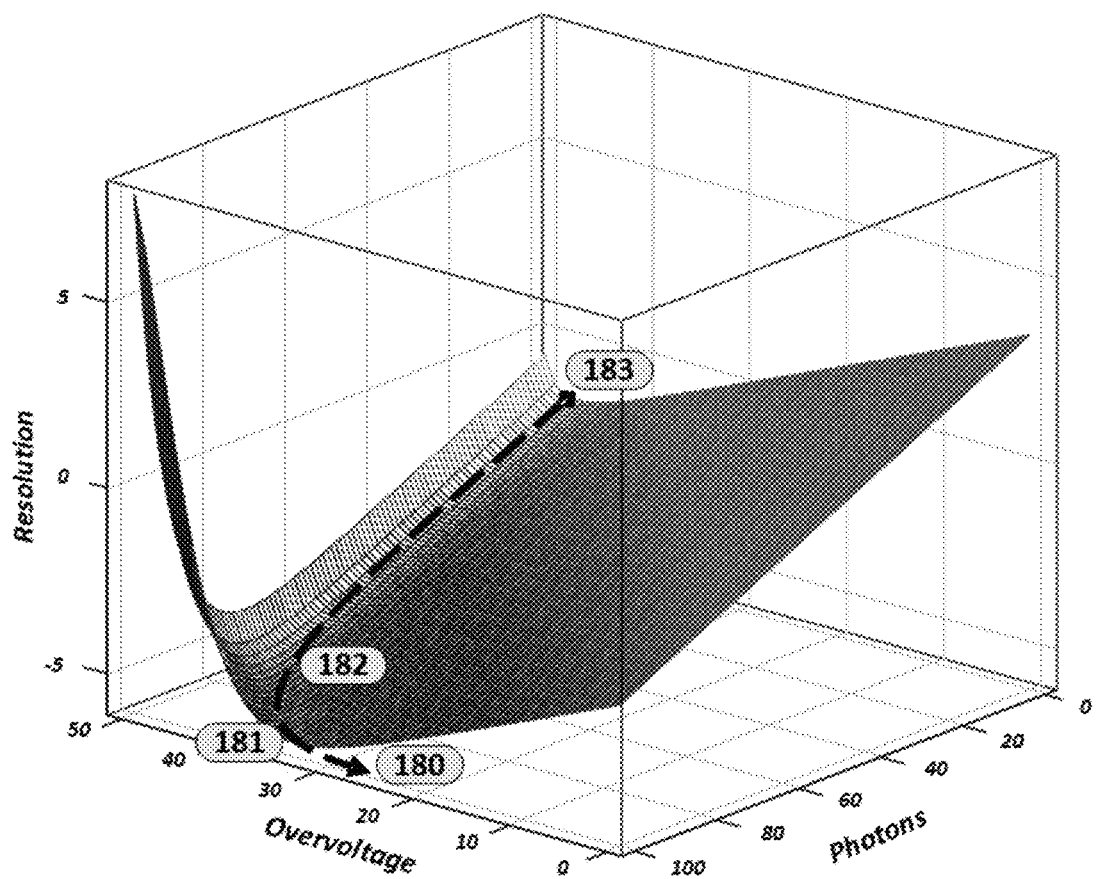
FIG. 16 is a 3D plot illustrating the relationship between resolution, overvoltage and number of photons.

In some embodiments an adaptive approach is used. It is based on the unique dependence of SiPM responsivity on bias voltage over a range of overvoltages FIG. 14, points 180, 181, 182, 183. A 3D plot illustrating the relationship between resolution, overvoltage and number of photons is shown in FIG. 16 with a contour minimum following the points marked 180, 181, 182, 183.

In some embodiments, an adaptive responsivity control may be described as follows:

Default operating voltage is set in correspondence with the optimal responsivity defined by the balance between an expectation to receive sub-optimal input signals and super-optimal ones.

Receiving and processing a sub-optimal signal, the bias voltage is shifted to a higher level depending on the signal strength up to the maximum operating voltage (e.g. 48 V, point 183, on FIG. 14)

Receiving and processing a super-optimal signal, the bias voltage is shifted to a lower level depending on the signal strength down to the minimum operating voltage of the limited Geiger mode (e.g. 38 V, Point 180, on FIG. 14).

Thus, each value of the detected signal forming an image is associated with the corresponding bias voltage and the responsivity of the SiPM at this point. It allows reconstruction of the image details with the optimal resolution in an extended dynamic range.

With respect to the packet of x-ray pulses used in this embodiment, the general algorithm described above is adjusted as follows:

During the ramp X-ray pulse, the intensity of light photon flux incident on SiPM increases over time depending on the attenuation of the X-rays, and then the SiPM output signal may or may not achieve a known saturation level;

Receiving and processing an output signal, the decision on adjustment of the SiPM responsivity is made for the next X-ray pulse within the packet;

If saturation is not observed, then the bias voltage is shifted to a higher level depending on the difference between the saturation level and the received maximum output signal;

If saturation is observed, then the bias voltage could be shifted to a lower level.

It should be noted that typical SiPM designs do not introduce considerable limitations on time required to change SiPM responsivity by changing its operating bias. In fact, this transient time is defined by the slowest RC time constant of the readout, namely, by the SiPM itself. The typical value of its total terminal capacitance is $C_{total}$~40 pF/mm$^2$ and the values of a pixel quenching resistor are $R_{quench}$~0.4 ... 0.7 MOhm (total $R_{total}$ is $N_{pixel}$ times lower as all pixels are in parallel), thus the RC time of the SiPM recharging is about equal to a well-known SiPM parameter—the pixel recovery time (dead time)—which is in the range from tens to hundreds of nanoseconds.

This feature of the SiPM allows this embodiment to utilize an adaptive control over SiPM responsivity on a tens of nanosecond scale, which is fast enough for the proposed application. It is worthwhile to note that similar control with an embodiment using a vacuum PMT would require much longer times because the recharging circuit includes high resistivity voltage dividers for biasing the PMT dynodes.

In general, the internal processes of the SiPM influenced by abrupt change of bias voltage are much faster, with a characteristic time of spatial re-distribution of internal electric field and free electrons and holes that is equal to the Maxwell relaxation time (picosecond range). However, the transient process toward a new steady-state distribution of trapped charge and occupation of deep level traps could take much more time, depending on the activation energy of the traps. Nevertheless, ongoing advances in modern SiPM technology show significant overall progress including, in particular, reduction of deep level trap density and the associated afterpulsing effect from 30% to <3% [K. Yamamoto, "New Developments of Hamamatsu on MPPC", in 2nd SiPM Advanced Workshop, Geneva, Switzerland, 24-26 Mar., 2014].

Feedback Mechanism

In some embodiments there are multiple feedback loops in operation. In some embodiments these feedback loops operate independently from each other. The first feedback loop operated between packets of pulses controls the length of the subsequent packet of x-ray pulses (i.e. maximum end-point energy of packet) based on the measured response of the detectors in the present packet of pulses. The feedback signal is based on the attenuation measured by all pixels of the detector array in the latest slice. By using this feedback, it will be possible to reduce dose. Observation of saturation in the measured signal from one packet of x-ray pulses is used to either shorten the next packet of pulses if it is measured that the detector output has become saturated, or extend the packet of pulses for the next packet if it is measured that the detector output has not become saturated or has displayed less saturation and the present packet is operating under a shortened packet mode, or make no change in packet duration for the next packet if the detector conditions are consistent with the present packet duration.

In some embodiments a second feedback loop operates between pulses within a packet. This feedback loop controls the SiPM bias voltage. This feedback control adjusts the gain to keep the SiPM out of saturation. It is a very fast feedback, with adjustment time typically within about several tens of nanoseconds. It is usually individual and independent for each SiPM circuit and in some embodiments controlled by a fast pixel processor, e.g. a Field Programmable Gate Array (FPGA). By using this feedback, it is possible to increase the dynamic range of detectors, and as a result—to improve system parameters such as material discrimination over a range of object thicknesses. This feedback signal controls the responsivity of the SiPM.

In some embodiments the linac repetition rate control based on speed of cargo. The relationship between linac repetition rate F (pulses per second), speed of cargo V (meters per second), horizontal detector pixel size d (meters) and sampling coefficient k, can be described as:
$F=V*k/d$. Therefore, for given sampling coefficient linac repetition rate is proportional to cargo speed.
If $k=1$, it is 100% sampling regime; if $k=0.5$ it is undersampling (50% sampling); if $k=2$, it is oversampling.
For example, let us have detector pixel size 1 cm=0.01 m, V=36 km/h=10 m/s. Then, if 100% sampling is needed (full imaging of cargo), the linac repetition rate needs to be $F=10*1/0.01=1000$ pps. For speed 5 m/s and $k=1$: $F=5*1/0.01=500$ pps. If 75% sampling will be sufficient, for speed 10 m/s, $F=10*0.75/0.01=750$ pps.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

Unless specifically stated otherwise, discussions herein using words such as "processing," "computing," "calculating," "determining," "presenting," "displaying," or the like may refer to actions or processes of a machine (e.g., a computer or other device having one or more processors) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" or "some embodiments" means that a particular element, feature, structure, or characteristic described in connection with the embodiment is included in at least one embodiment. The appearances of the phrase "in one embodiment" or "in some embodiments" in various places in the specification are not necessarily all referring to the same embodiment or same embodiments.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed is:

1. A system for inspecting an object, the system comprising:
   an X-ray generator producing an X-ray beam incident upon the object, the X-ray generator including a modulatable source of electrons, a target to which the electrons are accelerated, at which target X-rays are generated by a Bremsstrahlung process, and a collimator that forms the beam from the X-rays generated at the target;
   a detector array, formed of silicon photomultipliers, each photomultiplier associated with a distinct detector pixel, disposed to receive X-rays that have been transmitted through the object and to produce an output indicative of X-rays that have been transmitted through the object;
   a source controller system coupled to the X-ray generator, the source controller system configured:
   (i) to modulate the electrons, and consequently the beam of X-rays, into a temporal sequence of packets of substantially more than three pulses in a given packet, each successive pulse in the packet being of a uniform duration and spaced apart in time from its predecessor pulse by a substantially uniform nonzero gap, wherein an end-point energy of each successive X-ray pulse in a given packet is modified over that of its predecessor pulse, so as to provide in the given packet a train of pulses having a defined energy envelope over time; and
   (ii) to control electron current associated with each pulse in a manner wherein the higher the energy associated with a given pulse of the given packet, the lower the electron current provided in connection with the given pulse; and
   a processor system, coupled to the detector array, the processor system configured to adjust, between each of the successive pulses in any given packet, bias voltage on each of the silicon photomultipliers to separately control responsivity of each silicon photomultiplier in the detector array in a manner so as to maintain sensitivity of each detector pixel to X-ray photons while also preventing saturation of such silicon photomultiplier.

2. A system for inspecting an object according to claim 1, wherein the defined energy envelope is an upward sloping ramp over the sequence of pulses in the given packet.

3. A system according to claim 2, wherein the processor system is further configured to adjust bias voltage, on any given one of the silicon photomultipliers for a successive pulse in a given packet, based on an output signal of the given silicon photomultiplier in response to an immediately preceding pulse in the given packet.

4. A system for inspecting an object according to claim 1, wherein the processor is further configured to separate the output of the detector array, attributable to the given packet of X-ray pulses, into first and second temporal bands corresponding to first and second distinctive end-point energies associated with the respective temporal bands, and to employ dual-energy processing of the respective bands to perform atomic number analysis of the object at a corresponding inspection location thereof.

5. A system for inspecting an object according to claim 1, wherein the processor system is further configured to adjust, via a feedback loop between the detector array output and the X-ray generator, in a manner responsive to the detector array output from an immediately preceding X-ray packet, in relation to the given packet, the number of pulses in the given packet so as to supply, to the object, an amount of X-ray energy sufficient for traversing the object and registering on the detector array, so that the detector array dynamically controls end-point energy of each packet of X-rays based on measured attenuation of a preceding packet.

6. A system for inspecting an object according to claim 1, further comprising:
   a material discrimination processor coupled to the detector array and configured, to determine, on a pixel by pixel basis, based on a detector channel output from a preceding X-ray packet, appropriate energy windows for material discrimination that depend on cargo attenuation.

7. A system according to claim 1, wherein the X-ray generator includes a linac.

8. A system according to claim 1, wherein the detector array includes an array of Scintillation detectors.

9. A system according to claim 1, wherein the detector array includes an array of Cherenkov detectors.

10. A system according to claim 1, wherein the detector array includes an array of compensated Scintillation-Cherenkov detectors.

11. A system according to claim 1, wherein the source controller system is configured to modulate the electrons and consequently the beam of X-rays into a temporal sequence of packets of at least eight pulses in the given packet.

* * * * *